US00PP32509P2

(12) United States Plant Patent
Schroll

(10) Patent No.: US PP32,509 P2
(45) Date of Patent: Nov. 24, 2020

(54) ***HYDRANGEA* PLANT NAMED 'SCHROLL93-13-01'**

(50) Latin Name: *Hydrangea macrophylla*
Varietal Denomination: SCHROLL93-13-01

(71) Applicant: Soren Schroll, Odense SV (DK)

(72) Inventor: Soren Schroll, Odense SV (DK)

(73) Assignee: SCHROLL MANAGEMENT ApS, Odense SV (DK)

( * ) Notice: Subject to any disclaimer, the term of this patent is extended or adjusted under 35 U.S.C. 154(b) by 0 days.

(21) Appl. No.: 16/873,038

(22) Filed: Jan. 21, 2020

(51) Int. Cl.
*A01H 5/00* (2018.01)
*A01H 6/48* (2018.01)

(52) U.S. Cl.
USPC ..... Plt./250

(58) Field of Classification Search
USPC ..... Plt./250
See application file for complete search history.

*Primary Examiner* — Susan McCormick Ewoldt
(74) *Attorney, Agent, or Firm* — C. A. Whealy

(57) ABSTRACT

A new and distinct cultivar of *Hydrangea* plant named 'SCHROLL93-13-01', characterized by its compact, upright and mounded plant habit; moderately vigorous growth habit; freely branching habit and moderately strong stems; dark green-colored leaves; mophead-type inflorescences with light red purple-colored sterile flowers; when "blued", that is, treated with aluminum sulfate, sterile flowers are light purple in color; long flowering period; good postproduction quality and longevity and relatively good garden performance.

3 Drawing Sheets

Figure 1:
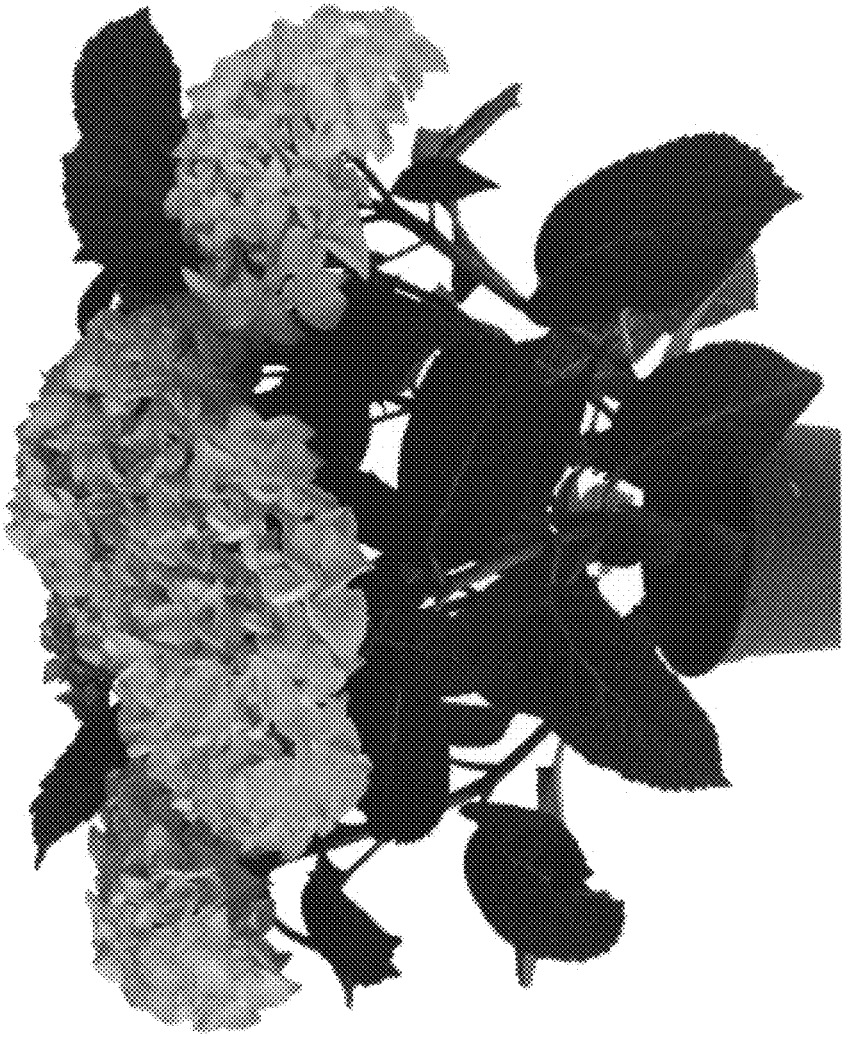

Botanical designation: *Hydrangea macrophylla.*
Cultivar denomination: 'SCHROLL93-13-01'.

BACKGROUND OF THE INVENTION

The present invention relates to a new and distinct cultivar of *Hydrangea* plant, botanically known as *Hydrangea macrophylla* and hereinafter referred to by the name 'SCHROLL93-13-01'.

The new *Hydrangea* plant is a product of a planned breeding program conducted by the Inventor in Aarslev, Denmark. The objective of the breeding program was to develop new container-type *Hydrangea* plants with strong stems, early flowering response and attractive leaf and flower coloration.

The new *Hydrangea* plant originated from a cross-pollination during the early spring of 2013 of a proprietary selection of *Hydrangea macrophylla* identified as code number 78-00, not patented, as the female, or seed, parent with a proprietary selection of *Hydrangea macrophylla* identified as code number 080108, not patented, as the male, or pollen, parent. The new *Hydrangea* plant was discovered and selected by the Inventor in February, 2015 as a flowering plant from within the progeny of the stated cross-pollination in a controlled greenhouse environment in Aarslev, Denmark.

Asexual reproduction of the new cultivar by softwood cuttings in Aarslev, Denmark since the spring of 2015 has shown that the unique features of this new *Hydrangea* plant are stable and reproduced true to type in successive generations of asexual reproduction.

SUMMARY OF THE INVENTION

Plants of the new *Hydrangea* have not been observed under all possible combinations of environmental conditions and cultural practices. The phenotype may vary somewhat with variations in environmental conditions such as temperature and light intensity without, however, any variance in genotype.

The following traits have been repeatedly observed and are determined to be the unique characteristics of 'SCHROLL93-13-01'. These characteristics in combination distinguish 'SCHROLL93-13-01' as a new and distinct *Hydrangea* plant:

1. Compact, upright and mounded plant habit.
2. Moderately vigorous growth habit.
3. Freely branching habit and moderately strong stems.
4. Dark green-colored leaves.
5. Mophead-type inflorescences with light red purple-colored sterile flowers; when "blued", that is, treated with aluminum sulfate, sterile flowers are light purple in color.
6. Long flowering period.
7. Good postproduction quality and longevity and relatively good garden performance.

Plants of the new *Hydrangea* differ primarily from plants of the female selection parent in the following characteristics:

1. Plants of the new *Hydrangea* are stronger than plants of the female parent selection.
2. Plants of plants of the new *Hydrangea* flower earlier than plants of the female parent selection.
3. Plants of the new *Hydrangea* and the female parent selection differ in sterile flower color as sterile flowers of plants of the new *Hydrangea* are red purple in color whereas sterile flowers of plants of the female parent selection are white and dark pink in color.
4. Plants of the new *Hydrangea* tolerate higher light levels than plants of the female parent selection.

Plants of the new *Hydrangea* differ primarily from plants of the male selection parent in sterile flower color as sterile flowers of plants of the new *Hydrangea* are red purple in color and when "blued", light purple, whereas sterile flowers of plants of the male parent selection are soft pink in color and when "blued", light blue in color. In addition, plants of the new *Hydrangea* are more tolerant to high light levels, wind and rain than plants of the male parent selection.

Plants of the new *Hydrangea* can be compared to plants of *Hydrangea macrophylla* 'H213901', disclosed in U.S. Plant Pat. No. 26,221. Plants of the new *Hydrangea* differ primarily from plants of 'H213901' in the following characteristics:

1. Plants of the *Hydrangea* are more compact than and not as vigorous as plants of 'H213901'.
2. Plants of the *Hydrangea* force faster than plants of 'H213901'.
3. Sepals of sterile flowers of the new *Hydrangea* are not as undulate as sepals of sterile flowers of 'H213901'.
4. Plants of the new *Hydrangea* and 'H213901' differ in sterile flower color as sterile flowers of plants of the new *Hydrangea* are lighter in color than sterile flowers of plants of 'H213901'.

Plants of the new *Hydrangea* can be compared to plants of *Hydrangea macrophylla* 'H213906', disclosed in U.S. Plant Pat. No. 26,509. Plants of the new *Hydrangea* differ primarily from plants of 'H213906' in sterile flower color as when "blued", sterile flowers of plants of the new *Hydrangea* are light purple in color whereas when "blued", sterile flowers of plants of 'H213906' are blue in color.

BRIEF DESCRIPTION OF THE PHOTOGRAPHS

The accompanying colored photographs illustrate the unique appearance of the new *Hydrangea* plant showing the colors as true as it is reasonably possible to obtain in colored reproductions of this type. Colors in the photographs may differ from the color values cited in the detailed botanical description which accurately describe the colors of the new *Hydrangea* plant.

The photograph on the first sheet (FIG. 1 of 3) comprises a side perspective view of a typical flowering plant of 'SCHROLL93-13-01' grown in a container that has not been "blued".

Figure 2:
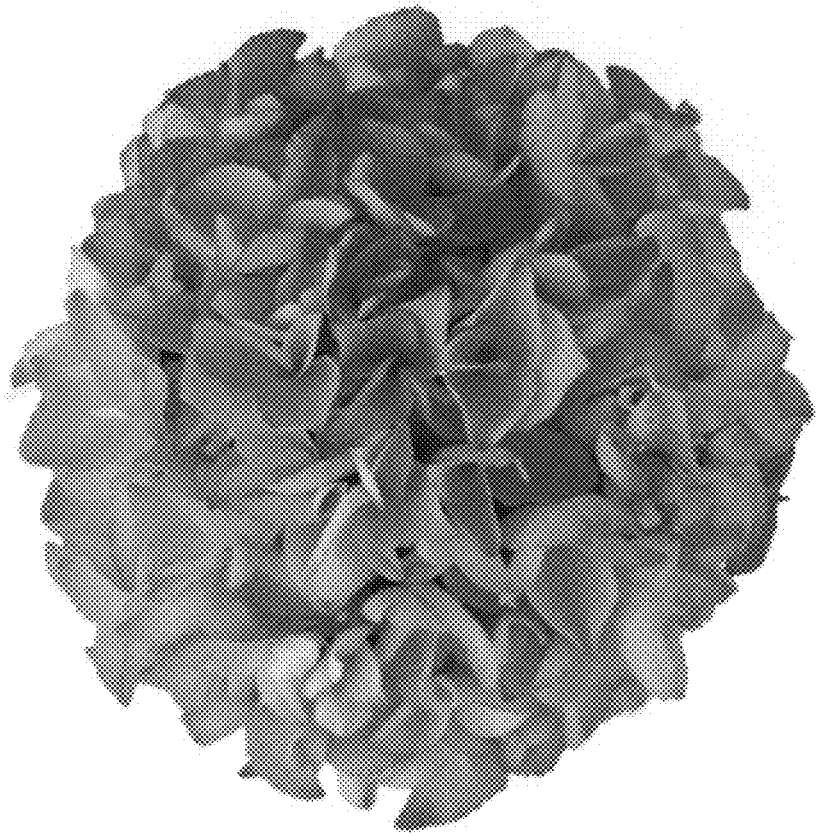

The photograph on the second sheet (FIG. 2 of 3) is a close-up view of a typical inflorescence of 'SCHROLL93-13-01' that has not been "blued".

Figure 3:
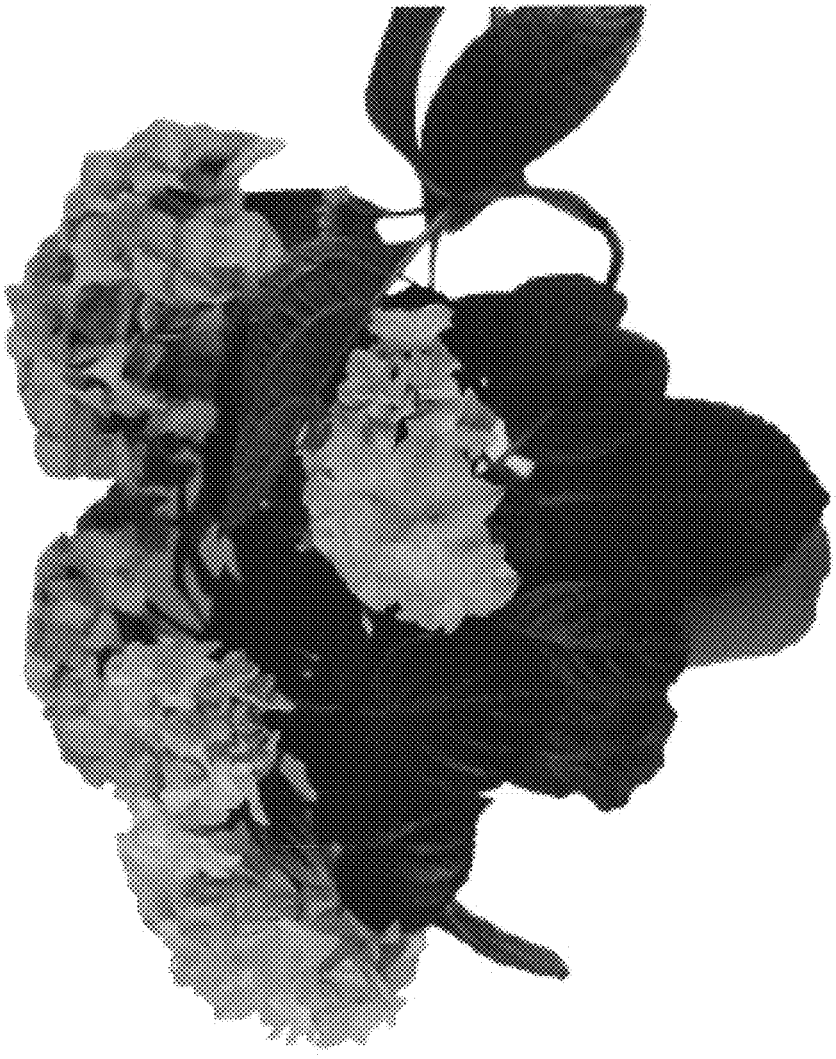

The photograph on the third sheet (FIG. 3 of 3) is a close-up view of a typical inflorescence of 'SCHROLL93-13-01' that has been "blued".

DETAILED BOTANICAL DESCRIPTION

Plants used in the aforementioned photographs and in the following description were grown during the spring in 13-cm containers in a glass-covered greenhouse in Aarslev, Denmark and under cultural practices typical of commercial *Hydrangea* production. Plants of the new *Hydrangea* were pinched two times and were one year old when the photographs and description were taken. During the production of the plants, day temperatures ranged from 15° C. to 25° C. and night temperatures ranged from 10° C. to 20° C. and light levels ranged from 40 to 50 klux. In the following description, color references are made to The Royal Horticultural Society Colour Chart, 2007 Edition, except where general terms of ordinary dictionary significance are used.

Botanical description: *Hydrangea macrophylla* 'SCHROLL93-13-01'.

Parentage:

*Female, or seed, parent*.—Proprietary selection of *Hydrangea macrophylla* identified as code number 78-00, not patented.

*Male, or pollen, parent*.—Proprietary selection of *Hydrangea macrophylla* identified as code number 080108, not patented.

Propagation:

*Type cutting*.—By softwood cuttings.

*Time to initiate roots, summer*.—About two weeks at temperatures about 19° C. to 22° C.

*Time to initiate roots, winter*.—About three weeks at temperatures about 18° C. to 20° C.

*Time to produce a rooted young plant, summer*.—About four weeks at temperatures about 18° C. to 20° C.

*Time to produce a rooted young plant, winter*.—About five weeks at temperatures about 18° C. to 20° C.

*Root description*.—Medium in thickness, fibrous; white, close to 158C, in color.

*Rooting habit*.—Freely branching; medium density.

Plant description:

*Plant and growth habit*.—Perennial subshrub; compact, upright and mounded plant habit; broadly inverted triangle; freely branching habit with about seven to ten lateral branches developing per plant; moderately strong lateral branches; moderately vigorous growth habit.

*Plant height*.—About 28 cm.

*Plant diameter or area of spread*.—About 45 cm.

*Lateral branches*.—Length: About 18 cm to 21 cm. Diameter: About 4 mm to 6 mm. Internode length: About 6 cm to 10 cm. Strength: Moderately strong, sturdy. Texture: Smooth, glabrous. Color, developing: Close to 144A to 144B. Color, developed: Close to 144A to 144B and at the nodes, close to 79A. Lenticels: Sparse, close to 79A in color.

Leaf description:

*Arrangement*.—Opposite, decussate; simple.

*Length*.—About 10 cm to 12 cm.

*Width*.—About 6.5 cm to 8.5 cm.

*Shape*.—Ovate.

*Apex*.—Apiculate to cuspidate.

*Base*.—Obtuse.

*Margin*.—Serrate.

*Texture, upper surface*.—Smooth, glabrous.

*Texture, lower surface*.—Rugose, glabrous.

*Venation pattern*.—Pinnate, reticulate.

*Color*.—Developing and fully expanded leaves, upper surface: Close to N137A; venation, close to 145C to 145D. Developing and fully expanded leaves, lower surface: Close to 137A to 137B; venation, close to 145C to 145D.

*Petioles*.—Length: About 3 cm to 5 cm. Diameter: About 3 mm to 5 mm. Strength: Strong. Texture, upper and lower surfaces: Smooth, glabrous. Color, upper surface: Close to 144A. Color, lower surface: Close to 144B.

Inflorescence & flower description:

*Flower type and habit*.—Showy single sterile and inconspicuous single fertile flowers arranged on terminal mophead-type panicles; panicles globular in overall shape; fertile flowers face upright to outwardly and sterile flowers face mostly upright to outwardly depending on their position on the inflorescence; early flowering habit, plants begin flowering about eight to ten weeks after forcing period.

*Natural flowering season*.—Long flowering period, continuous flowering from August until frost in Northern Europe.

*Flower longevity, fertile flowers*.—Flowers last about one month on the plant; fertile flowers not persistent.

*Flower longevity, sterile flowers*.—Flowers last about four months on the plant; sterile flowers persistent.

*Quantity of flowers*.—Freely flowering habit with about 25 fertile flowers and about 130 sterile flowers per panicle.

*Fragrance*.—None detected.

*Panicle height*.—About 8 cm to 9 cm.

*Panicle diameter*.—About 14 cm to 16 cm.

*Flower diameter, fertile flowers*.—About 6 mm to 7 mm.

*Flower depth (height), fertile flowers*.—About 3 mm to 4 mm.

*Flower diameter, sterile flowers*.—About 6 cm.

*Flower depth (height), sterile flowers*.—About 1.5 cm.

*Flower shape, fertile flowers*.—Spherical.

*Flower shape, sterile flowers*.—Rounded, flat to bending upwardly.

*Flower buds, fertile flowers*.—Length: About 3 mm. Diameter: About 3 mm. Shape: Spherical. Color: Close to 143B; margins, close to N57C.

*Flower buds, sterile flowers*.—Length: About 3 mm. Diameter: About 3 mm. Shape: Spherical. Color: Close to 145B.

*Petals, fertile flowers*.—To date, petal development on fertile flowers of plants of the new *Hydrangea* have not been observed.

*Petals, sterile flowers*.—Quantity and arrangement: If present, about four in a single whorl. Length: About 3 mm. Width: About 2 mm. Shape: Ovate. Apex: Acute. Base: Truncate. Margin: Entire. Texture, upper and lower surfaces: Smooth, glabrous. Color: When opening, upper and lower surfaces: Close to 65A; when "blued", close to N89D. Fully opened, upper and lower surfaces: Close to 63C; when "blued", close to 100B; margins becoming closer to NN155D with development.

*Sepals, fertile flowers*.—Quantity and arrangement: About five in a single whorl. Length: About 2 mm to 3 mm. Width: About 1 mm to 2 mm. Shape: Deltoid. Apex: Acute. Base: Cuneate. Margin: Entire. Texture, upper surface: Smooth, glabrous. Texture, lower surface: Pilose. Color: When opening, upper and lower surfaces: Close to 65A; when "blued", close to 149B. Fully opened, upper and lower surfaces: Close to 65A; when "blued", close to 149B; colors do not change with development.

*Sepals, sterile flowers*.—Quantity and arrangement: Four in a single whorl. Length: About 2.5 cm. Width: About 2.5 cm. Shape: Deltoid to ovate. Apex: Retuse. Base: Broadly cuneate. Margin: Entire. Texture, upper surface: Smooth to slightly rippled, glabrous. Texture, lower surface: Smooth, glabrous. Color: When opening, upper and lower surfaces: Close to 1 C to 1D; color does not change when "blued". Fully opened, upper surface: Close to N57C; when "blued", close to between N78C and 77C; with development, color becoming closer to 55A and towards the base, close to 145B and when "blued", becoming closer to between 75A and 77B. Fully opened, lower surface: Close to 62C; when "blued", close to 75A to 75B; with development, color becoming closer to 54A to 54C and towards the base, close to 145B and when "blued", becoming closer to 75B to 75C.

*Pedicels, fertile flowers*.—Length: About 1 cm. Diameter: About 1 mm. Strength: Strong. Aspect: Upright to outwardly. Texture: Pubescent. Color: Close to 64B; when "blued", close to 150B.

*Pedicels, sterile flowers*.—Length: About 3.5 cm. Diameter: About 2 mm. Strength: Moderately strong. Aspect: Upright to almost horizontal. Texture: Sparsely pubescent. Color: Close to 58A; when "blued", close to 150A.

*Reproductive organs, fertile flowers*.—Stamens: Quantity per flower: About ten. Filament length: About 1 mm. Filament color: Close to N57A. Anther length: About 1 mm. Anther shape: Ovate. Anther color: Close to 64B. Pollen amount: Abundant. Pollen color: Close to 155C. Pistils: Pistil quantity per flower: About three. Pistil length: Less than 1 mm. Stigma shape: Ovate. Stigma color: Close to N57A. Style length: About 1 mm. Style color: Close to 63C. Ovary color: Close to 63C.

*Reproductive organs, sterile flowers*.—Stamens: Quantity per flower: About eight to ten. Filament length: About 2 mm to 3 mm. Filament color: Close to N57A. Anther length: About 1 mm to 2 mm. Anther shape: Ovate. Anther color: Close to 64B. Pollen amount: Scarce. Pollen color: Close to 155C. Pistils: Pistil quantity per flower: If present, three. Pistil length: About 1 mm to 2 mm. Stigma shape: Oblong. Stigma color: Close to 59C. Style length: Less than 1 mm. Style color: Close to 58A. Ovary color: Close to 58A.

*Seeds (present on fertile flowers only)*.—Quantity per fertile flower: About 30 to 1,000. Length: About 0.5 mm. Diameter: About 0.1 mm. Color: Close to 200C.

Pathogen & pest resistance: To date, plants of the new *Hydrangea* have not been observed to be resistant to pathogens and pests common to *Hydrangea* plants.

Temperature tolerance: Plants of the new *Hydrangea* have been shown to be tolerant to temperatures ranging from about 3° C. to 38° C.

It is claimed:

1. A new and distinct *Hydrangea* plant named 'SCHROLL93-13-01' as illustrated and described.

* * * * *